US006989434B1

(12) United States Patent
Gebeyehu et al.

(10) Patent No.: US 6,989,434 B1
(45) Date of Patent: Jan. 24, 2006

(54) REAGENTS FOR INTRACELLULAR DELIVERY OF MACROMOLECULES

(75) Inventors: Gulilat Gebeyehu, Silver Spring, MD (US); Joel A. Jessee, Mt. Airy, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/326,106

(22) Filed: Jun. 4, 1999

Related U.S. Application Data

(63) Continuation of application No. 08/195,866, filed on Feb. 11, 1994, now Pat. No. 6,075,012.

(51) Int. Cl.
*A61K 38/00* (2006.01)
*C07H 1/00* (2006.01)
*A00N 37/18* (2006.01)
*A01N 43/04* (2006.01)

(52) U.S. Cl. .................... 530/300; 536/1.11; 536/18.7; 536/123.1; 514/2; 514/44; 514/23

(58) Field of Classification Search ................. 514/44, 514/2; 530/300, 350; 536/1.11, 4.1, 18.1, 536/18.5, 18.7, 22.1
See application file for complete search history.

(56) References Cited

U.S. PATENT DOCUMENTS

| | | | |
|---|---|---|---|
| 2,901,461 A | 8/1959 | Auerbach et al. | 260/47 |
| 3,152,188 A | 10/1964 | Kirkpatrick et al. | 260/584 |
| 4,235,871 A | 11/1980 | Papahadjopoulos et al. | 424/19 |
| 4,897,355 A | 1/1990 | Eppstein et al. | 435/240.2 |
| 4,946,787 A | 8/1990 | Eppstein et al. | 435/240.2 |
| 5,049,386 A | 9/1991 | Eppstein et al. | 424/427 |
| 5,165,925 A | 11/1992 | Leong | 424/88 |
| 5,171,678 A | 12/1992 | Behr et al. | 435/172.3 |
| 5,208,036 A | 5/1993 | Eppstein et al. | 424/450 |
| 5,279,833 A | 1/1994 | Rose | 424/450 |
| 5,283,185 A | 2/1994 | Epand et al. | 435/172.3 |
| 5,334,761 A | 8/1994 | Gebeyehu et al. | 564/197 |
| 5,455,335 A | 10/1995 | Kahne et al. | 536/5 |
| 5,459,127 A | 10/1995 | Felgner et al. | 514/7 |
| 5,521,291 A | 5/1996 | Curiel et al. | 530/391.7 |
| 5,545,412 A | 8/1996 | Eppstein et al. | 424/450 |
| 5,550,289 A | 8/1996 | Eppstein et al. | 564/293 |
| 5,578,475 A | 11/1996 | Jessee | 435/172.3 |
| 5,583,198 A | 12/1996 | Whittaker | 530/345 |
| 5,589,466 A | 12/1996 | Felgner et al. | 514/44 |
| 5,595,897 A | 1/1997 | Midoux et al. | 435/172.3 |
| 5,627,159 A | 5/1997 | Shih et al. | 514/44 |
| 5,635,487 A | 6/1997 | Wolff et al. | 514/44 |
| 5,650,096 A | 7/1997 | Harris et al. | 252/357 |
| 5,674,908 A | 10/1997 | Haces et al. | 514/642 |
| 5,693,509 A | 12/1997 | Cotten et al. | 435/172.3 |
| 5,703,055 A | 12/1997 | Felgner et al. | 514/44 |
| 5,719,131 A | 2/1998 | Harris et al. | 514/44 |
| 5,736,392 A | 4/1998 | Hawley-Nelson et al. | 435/320.1 |
| 5,744,335 A | 4/1998 | Wolff et al. | 435/172.3 |
| 5,753,613 A | 5/1998 | Ansell et al. | 514/2 |
| 5,780,053 A | 7/1998 | Ashley et al. | 424/450 |
| 5,783,565 A | 7/1998 | Lee et al. | 514/44 |
| 5,785,992 A | 7/1998 | Ansell et al. | 424/450 |
| 5,795,587 A | 8/1998 | Gao et al. | 424/450 |
| 5,827,703 A | 10/1998 | Debs et al. | 435/172.3 |
| 5,830,430 A | 11/1998 | Unger et al. | 424/1.21 |
| 5,830,878 A | 11/1998 | Gorman et al. | 514/44 |
| 5,834,439 A | 11/1998 | Haces et al. | 514/42 |
| 5,840,710 A | 11/1998 | Lee et al. | 514/44 |
| 5,854,224 A | 12/1998 | Lockett et al. | 514/44 |
| 5,861,397 A | 1/1999 | Wheeler | 514/247 |
| 5,869,606 A | 2/1999 | Whittaker | 530/345 |
| 5,906,922 A | 5/1999 | Whittaker et al. | 435/69.1 |
| 5,908,635 A | 6/1999 | Thierry | 424/450 |
| 5,908,777 A | 6/1999 | Lee et al. | 435/320 |
| 5,935,936 A | 8/1999 | Fasbender et al. | 514/44 |
| 5,948,767 A | 9/1999 | Scheule et al. | 514/44 |
| 5,948,925 A | 9/1999 | Keynes et al. | 552/540 |
| 6,020,202 A | 2/2000 | Jessee | 435/458 |
| 6,051,429 A | 4/2000 | Hawley-Nelson et al. | 435/458 |
| 6,086,913 A | 7/2000 | Tam et al. | 424/450 |
| 6,110,662 A | 8/2000 | Foung et al. | 435/5 |
| 6,110,916 A | 8/2000 | Haces et al. | 514/252.11 |
| 6,214,804 B1 | 4/2001 | Felgner et al. | 514/44 |
| 6,376,248 B1 | 4/2002 | Hawley-Nelson et al. | 435/458 |
| 6,387,395 B1 | 5/2002 | Eppstein et al. | 424/450 |
| 6,399,663 B1 | 6/2002 | Haces et al. | 514/642 |
| 2002/0077305 A1 | 6/2002 | Jessee et al. | 514/44 |

(Continued)

FOREIGN PATENT DOCUMENTS

EP          0 394 111         10/1990

(Continued)

OTHER PUBLICATIONS

Sigma Chemical Catalog, Sigma Chemical Company, St Louis Missouri, pp. 868 and 1649-1657, 1990.*

(Continued)

*Primary Examiner*—Ardin H. Marschel
(74) *Attorney, Agent, or Firm*—Greenlee, Winner and Sullivan, P.C.

(57) ABSTRACT

The present invention provides certain cationic lipids containing stigmasterol, ergosterol and cholic acid groups. Compounds of the invention are useful, either alone or in combination with other lipid aggregate-forming components (e.g., DOPE, DOSPA, DOTMA or cholesterol) for formulation into liposomes or other lipid aggregates. Such aggregates are cationic, and able to form stable complexes with anionic macromolecules, such as nucleic acids. The cationic lipids of the invention are useful in methods of transfecting cells, particularly to introduce nucleic acids into cells. The invention also related to kits for the preparation of lipid aggregates and to lipid aggregates and compositions for transfection of cells.

27 Claims, No Drawings

U.S. PATENT DOCUMENTS

| | | | |
|---|---|---|---|
| 2002/0086849 A1 | 7/2002 | Gebeyehu et al. | 514/44 |
| 2002/0156049 A1 | 10/2002 | Haces et al. | 514/79 |
| 2003/0069173 A1 | 4/2003 | Hawley-Nelson et al. | 514/8 |

FOREIGN PATENT DOCUMENTS

| | | |
|---|---|---|
| EP | 0 846 680 A1 | 6/1998 |
| FR | 1567214 | 5/1969 |
| WO | WO 90/11092 | 10/1990 |
| WO | 91/15501 | 10/1991 |
| WO | 91/16024 | 10/1991 |
| WO | WO 91/17424 | 11/1991 |
| WO | WO 93/03709 | 3/1993 |
| WO | WO 93/05162 | 3/1993 |
| WO | WO 93/14778 | 8/1993 |
| WO | WO 94/27435 | 12/1994 |
| WO | WO 95/02698 | 1/1995 |
| WO | WO 95/17373 | 6/1995 |
| WO | WO 96/40961 | 12/1996 |
| WO | WO 97/42819 | 11/1997 |
| WO | WO 98/02190 | 1/1998 |
| WO | WO 98/14439 | 4/1998 |
| WO | WO 98/19709 | 5/1998 |
| WO | WO 98/29541 | 7/1998 |
| WO | WO 98/40502 | 9/1998 |
| WO | WO 99/02190 | 1/1999 |
| WO | WO 99/29712 | 6/1999 |
| WO | WO 00/27795 | 5/2000 |
| WO | WO 00/58488 | 10/2000 |
| WO | WO 02/34879 | 5/2002 |

OTHER PUBLICATIONS

Sigma Chemical Catalog, Sigma Chemical Company, P.O. Box 14508, St. Louis, Missouri, p. 1066, 1990.*

Wood et al., Hypertension, vol. 7, No. 5, pp. 797-803, 1985.*

New Riverside University Dictionary Published by the Riverside Publishing Company, Houghton Mifflin Company, One Beacon Street, Boston, Massachusetts 02108) (1984), p. 1324.*

Biochemistry, by Lehninger Published by Worth Publishers, Inc., 70 Fifth Avenue, New York, New York, 10011 (1970) pp. 69-71, 98, 99, 227-229, and 233.*

Christensen et al., Biochemical and Biophysical Research Communications, vol. 155, No. 3, pp. 1278-1283 (1988).*

Chang et al., Biochemistry, vol. 14, No. 3, pp. 468-477 (1975).*

Barthel, F. et al. (1993), "Gene Transfer Optimization with Lipospermine-Coated DNA," DNA and Cell Biology 12(6): 553-560.

Behr, J.-P. et al. (1989), "Efficient gene transfer into mammalian primary endocrine cells with lipopolyamine-coated DNA," Proc. natl. Acad. Sci. USA 86:6982-6986.

Duzgunes, N. et al. (1989), "Fusion of Liposomes containing a Novel Cationic Lipid, N-[2,3-(Dioleyloxy)propyl]-N, N,N-trimethylammonium: Induction by Multivalent Anions and Asymmetric Fusion with Acidic Phospholipid Vesicles," Biochemistry 28:9179-9184.

Felgner, P.L. et al. (1987), "Lipofection: A highly efficient, lipid-mediated DNA-transfection procedure," Proc. Natl. Acad. Sci. USA 84:7413-7417.

Gao, X. et al. (1991), "A Novel Cationic Liposome Reagent for Efficient Transfection of Mammalian Cells," Biochim. Biophys. Res. Comm. 179:280-285.

Loeffler, J.-P. et al. (1993), "Gene Transfer into Primary and Established Mammalian Cell Lines with Lipopolyamine-Coated DNA," Methods Enzymol. 217:599-618.

Zhou, X. et al. (1991), "Lipophilic polylysines mediate efficient DNA transfection in mammalian cells," Biochim. Biophys. Acta 1065:8-14.

Sigma Chemical Catalog,(1990) Published by the Sigma Chemical Co., St. Louis, MO, pp. 560, 670 and 671.

Felgner et al. (1993) Keystone Symposium on Genetic Targeted Research and Therapeutics: Antisense and Gene Therapy, Keystone, CO; J. Cell. Biochem. Suppl. 0(17 Part E), p. 206, S306.

Lehninger (1970) Biochemistry (Published by Worth Publishers, Inc., New York, NY, pp. 69-71.

Sigma Chemical Catalog (1990) Published by the Sigma Chemical Co., St. Louis, MO, p. 1107.

Budker et al. (1997) "Protein/Amphipathic Polyamine Complexes Enable Highly Efficient Transfection with Minimal Toxicity" BioTechniques 23:139-147.

Behr, J-P. (Sep. 1994), "Gene Transfer with Synthetic Cationic Amphiphiles: Prospects for Gene Therapy," Bioconjug. Chem. 5:382-389.

Bottger, M. et al. (1988), "Condensation of vector DNA by the chromosomal protein HMGI results in efficient transfection," Biochim. Biophys. Acta 950:221-228.

Cotten, M. and Wagner, E. (Dec. 1993), "Non-viral approaches to gene therapy," Curr. Opin. Biotechnol. 4:705-710.

Giles, R.V. (2000), "Antisense oligonucleotide technology: From EST to therapeutics," Curr. Opin. Mol. Therap. 2:238-252.

Henkel and Cie. G.m.b.H. (Apr. 1970), abstract no. 68522p, "Low-foaming detergents containing bisquaternary compounds," Chem. Abst. 72(14):116.

Kaneda, Y. et al. (1989), "Increased Expression of DNA Cointroduced with Nuclear Protein in Adult Rat Liver," Science 243:375-378.

Murphy, A.L. (Jan. 1999), "Catch VP22: the hitch-hiker's ride to gene therapy?" Gene Therapy 6:4-5.

Neckers, L.M. (May 1993), "Cellular Internalization of Oligodeoxynucleotides," in Antisense Research and Applications, Crooke, S.T. and Leblue, B., eds., CRC Press, LLC, Boca Raton, FL, pp. 451-460.

Neurath, et al. (1990), "B cell epitope mapping of human immunodeficiency virus envelope glycoproteins with long (19- to 36-residue) synthetic peptides," J. Gen. Virol. 71: 85-95.

Rothenberg, M. et al. (1989), "Oligodeoxynucleotides as Anti-Sense Inhibitors of Gene Expression: Therapeutic Implications," J. Natl. Can. Inst. 81:1539-1544.

van der Krol, A.R. et al. (1988), "Modulation of Eukaryotic Gene Expression by Complementary RNA or DNA Sequences," Biotechniques 6:958-976.

Wixon, H.E. (1969), "Anionic detergentscontaining trialkylamine oxides as fabric softeners," Chem. Abstract, vol. 72, Abstracts No. 68523q, p. 116.

(Jan. 1993) Sigma Catalog, pp. 1028-1034.

Bennett, C.F. et al. (1992), "Cationic Lipids Enhance Cellular Uptake and Activity of Phosphorothioate Antisense Oligonucleotides," Mol. Pharm. 41:1023-1033.

Bond, V.C. and Wold, B. (Jun. 1987), "Poly-L-Ornithine-Mediated Transformation of Mammalian Cells," Mol. Cell. Biol. 7(6):2286-2293.

Chaney, W.G. et al. (1986), "High-Frequency Transfectionof CHO Cells Using Polybrene," Som. Cell Mol. Genet. 12(3): 237-244.

Dong, Y. et al. (1993), "Efficient DNA transfection of quiescent mammalian cells using poly-L-orinithine," Nucl. Acids Res. 21:771-772.

Donnelly-Roberts, D.L. and Lentz, T.L. (1991), "Structural and conformational similarity between synthetic peptides of curaremimetic neurotoxins and rabies virus glycoprotein," Mol. Brain Res. 11:107-113.

Duzgunes, N. and Felgner, P. (1993), "Intracellular Delivery of Nucleic Acids and Transcription Factors by Cationic Liposomes," Meth. Enzymol. 221:303-317.

Farhood, H. et al. (1992), "Effect of cationic cholesterol derivatives on gene transfer and protein kinase C activity," Biochim. Biophys. Acta 1111:239-246.

Felgner, P.L. and Holm, M. (Spring 1989), "Cationic Liposome-Mediated Transfection," Focus 11(2):21-25.

Felgner, P.L. (1993), "Cationic Lipid/Polynucleotide Condenstaes for In Vitro and In Vivo Polynucleotide Delivery—The Cytofectins," J. Liposome Res. 3(1):3-16.

Gao, X. and Huang, L. (1993), "Cationic Liposomes and Polymers for Gene Transfer," J. Liposome Res. 3(1):17-30.

Gao, X. and Huang, L. (1993), "Cytoplasmic expression of a reporter gene by co-delivery of T7 RNA polymerase and T7 promoter sequence with cationic liposomes," Nucl. Acids Res. 21(12):2867-2872.

Huang, L. and Zhou, F. (1992), "Liposome and Immunoliposome Mediated Delivery of Proteins and Peptides," *Targeting of Drugs 3—The Challenge of Peptides and Proteins*, Gregoriadis, G. and Florence, A.T. (eds.), Plenum Press, New York, NY, pp. 45-50.

Litzinger, D.C. and Huang, L. (1992), "Amphipathic poly (ethylene glycol) 5000-stabilized dioleoylphosphatidylethanolamine liposomes accumulate in spleen," Biochim. Biophys. Acta 1127:249-254.

Litzinger, D.C. and Huang, L. (1992), "Phosphatidylethanolamine liposomes: drug delivery, gene transfer and immunodiagnostic applications," Biochim. Biophys. Acta 1113:201-227.

Nabel, G.J. and Felgner, P.L. (May 1993), "Direct gene transfer for immunotherapy and immunization," Tibtech 11:211-215.

Nair, S. et al. (1992), "Class I restricted CTL recognition of a soluble protein delivered by liposomes containing lipophilic polylsines," J. Immun. Meth. 152:237-243.

Park, Y.S. and Huang, L. (1992), "Interaction of synthetic glycophospholipids with phospholipid bilayer membranes," Biochim Biophys. Acta 1112:251-258.

Park, Y.S. et al. (1992), "Some negatively charged phospholipid derivatives prolong the liposome circulation in vivo," Biochim. Biophys. Acta 1108:257-260.

Stegmann, T. et al. (1989), "Protein-Mediated Membrane Fusion," Ann. Rev. Biophys. Biophys. Chem. 18:187-211.

Stewart, M.J. et al. (1992), "Gene Transfer In Vivo with DNA-Liposome Complexes: Safety and Acute Toxicity in Mice," Human Gene Therapy 3:267-275.

Trubetskoy, V.S. et al. (1992), "Cationic liposomes enhance targeted delivery and expression of exogenous DNA mediated by N-terminal modified poly(L-lysine)-antibody conjugate in mouse lung endothelial cells," Biochim. Biophys. Acta 1131:311-313.

Trubetskoy, V.S. et al. (1992), "Use of N-Terminal Modified Poly(L-lysine)-Antibody Conjugate as a Carrier for Targeted Gene Delivery in Mouse Lung Endothelial Cells," Bioconjugate Chem. 3:323-327.

White, J.M. (1989), "Cell-to-cell fusion," Cell. Biol. 1:934-939.

White, J.M. (1990), "Viral and Cellular Membrane Fusion Proteins," Ann. Rev. Physiol. 52:675-697.

Zhou, X. and Huang, L. (1992), "Targeted delivery of DNA by liposomes and polymers," J. Controlled Release 19:269-74.

* cited by examiner

REAGENTS FOR INTRACELLULAR DELIVERY OF MACROMOLECULES

CROSS-REFERENCE TO RELATED APPLICATIONS

This application is a continuation of U.S. patent application Ser. No. 08/195,866 filed Feb. 11, 1994, now U.S. Pat. No. 6,075,012, which is incorporated by reference in its entirety herein to the extent not inconsistent herewith.

FIELD OF THE INVENTION

Cationic lipid compounds are disclosed, having utility in lipid aggregates for delivery of macromolecules and other compounds into cells. Also disclosed are compositions of cationic lipids and viral components or non-viral fusagenic compounds useful for enhancing transfection.

BACKGROUND OF THE INVENTION

Lipid aggregates such as liposomes have been found to be useful as agents for delivery to introduce macromolecules, such as DNA, RNA, protein, and small chemical compounds such as pharmaceuticals, to cells. In particular, lipid aggregates comprising cationic lipid components have been shown to be especially effective for delivering anionic molecules to cells. In part, the effectiveness of cationic lipids is thought to result from enhanced affinity for cells, many of which bear a net negative charge. Also in part, the net positive charge on lipid aggregates comprising a cationic lipid enables the aggregate to bind polyanions, such as nucleic acids. Lipid aggregates containing DNA are known to be effective agents for efficient transfection of target cells.

The structure of various types of lipid aggregates varies, depending on composition and method of forming the aggregate. Such aggregates include liposomes, unilamellar vesicles, multilameller vesicles, micelles and the like, having particle sizes in the nanometer to micrometer range. Methods of making lipid aggregates are by now well-known in the art. The main drawback to use of conventional phospholipid-containing liposomes for delivery is that the material to be delivered must be encapsulated and the liposome composition has a net negative charge which is not attracted to the negatively charged cell surface. By combining cationic lipid compounds with a phospholipid, positively charged vesicles and other types of lipid aggregates can bind DNA, which is negatively charged, can be taken up by target cells, and can transfect target cells. (Felgner, P. L. et al. (1987) Proc. Natl. Acad. Sci. USA 84:7413–7417; Eppstein, D. et al., U.S. Pat. No. 4,897,355.)

Cationic lipids useful for transfection and intracellular delivery of macromolecules generally contain the following four structural elements:

| Lipophilic group | Linker bond | Spacer arm | Cationic group |
| --- | --- | --- | --- |

The lipophilic group is a hydrophobic moiety which facilitates the insertion of the cationic amphiphile into the membranes of the cell or liposome. The lipophilic group serves as an anchor for the cationic group (usually ammonium) which is positively charged at neutral Ph, to attach to the surface of the cell or liposome. The spacer arm is typically a hydrophilic, 2 to 15-atom moiety which connects the cationic group to the lipophilic group via the linker bond. The linker bond is either an ether, ester, amide or other hydrolyzable bond.

A well-known cationic lipid disclosed in the prior art is N-[1-(2,3-dioleoyloxy)propyl]-N,N,N-trimethylammonium chloride (DOTMA). The structure of DOTMA is:

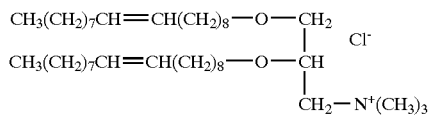

DOTMA by itself or in 1:1 combination with dioleoylphosphatidyl-ethanolamine (DOPE) is formulated into liposomes using standard techniques. Felgner, et al. supra demonstrated that such liposomes provided efficient delivery of nucleic acids to some types of cells. A DOTMA:DOPE (1:1) formulation is sold under the trade name LIPOFECTIN (Gibco/BRL: Life Technologies, Inc., Gaithersburg, Md.). Another commercially available cationic lipid is 1,2-bis(oleoyloxy)-3-3-(trimethylammonia) propane (DOTAP), which differs from DOTMA only in that the oleoyl moieties are linked via ester, rather than ether bonds to the propylamine. DOTAP is believed to be more readily degraded by target cells. A related group of prior art compounds differ from DOTMA and DOTAP in that one of the methyl groups of the trimethylammonium group is replaced by a hydroxyethyl group. Compounds of this type are similar to the Rosenthal Inhibitor (RI) of phospholipase A (Rosenthal, A. F. and Geyer, R. P. (1960) J. Biol. Chem. 235:2202–2206) which has stearoyl esters linked to the propylamine core. The dioleoyl analogs of RI are commonly abbreviated as DORI-ether and DORI-ester, depending on the linkage of the fatty acid moieties to the propylamine core. The hydroxy group can be used as a site for further functionalization, for example by esterification to carboxyspermine.

Another class of prior art compounds has been disclosed by Behr et al. (1989) Proc. Natl. Acad. Sci. USA 86:6982–6986; EPO publication 0 394 111 (Oct. 24, 1990), in which carboxyspermine has been conjugated to two types of lipids. The structures of 5-carboxyspermylglycine dioctadecylamide (DOGS) is:

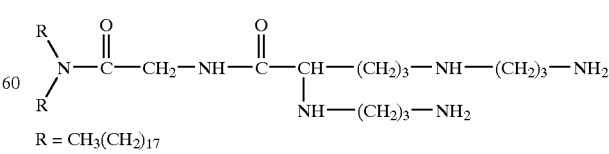

The structure of dipalmitoylphosphatidylethanolamine 5-carboxy-spermylamide (DPPES) is:

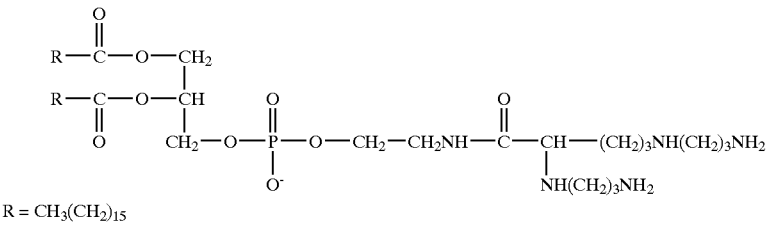

R = CH₃(CH₂)₁₅

Both DOGS and DPPES have been used to coat plasmids, forming a lipid aggregate complex that provides efficient transfection. The compounds are claimed to be more efficient and less toxic than DOTMA for transfection of some cell lines. DOGS is available commercially as TRANS-FECTAM™ (Promega, Madison, Wis.).

A cationic cholesterol derivative (DC-Chol) has been synthesized and formulated into liposomes in combination with DOPE. (Gao, X. and Huang, L. (1991) Biochim. Biophys. Res. Comm. 179:280–285) The compound's structure is

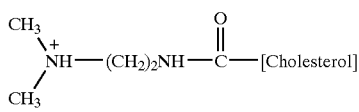

Liposomes formulated with DC-Chol are said to provide more efficient transfection and lower toxicity than DOTMA-containing liposomes for some cell lines.

Lipopolylysine, formed by conjugating polylysine to DOPE, has been reported to be especially effective for transfection in the presence of serum, a condition likely to be encountered in vivo (Zhou, X. et al. (1991) Biochim. Biophys. Acta 1065:8–14).

Despite advances in the field, a need remains for a variety of improved cationic lipid compounds. In particular, no single cationic lipid to date has been found to work well with all cell types. Since different cell types differ from one another in membrane composition, it is not surprising that different compositions and types of lipid aggregates are effective for different cell types, either for their ability to contact and fuse with target cell membranes, or for aspects of the transfer process itself. Besides content and transfer, other factors are of importance, for example, ability to form lipid aggregates suited to the intended purpose, toxicity to the target cell, stability as a carrier for the compound to be delivered, and ability to function in an in vivo environment. In addition, lipid aggregates can be improved by broadening the range of substances which can be delivered to cells. The cationic lipid compounds of the present invention have improved function with respect to several of the foregoing attributes. Compositions of the invention comprising cationic lipids in combination with viral components or non-viral fusagenic compounds are particularly useful for enhancing the efficiency of transfection and/or the range of delivery capabilities.

SUMMARY OF THE INVENTION

The present invention provides novel cationic lipids according to the general formula:

FORMULA I

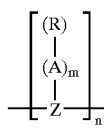

In the general formula (I),

R is $R_A$ or $R_B$, where $R_A$ is $C_{1-23}$ alkyl or alkenyl and $R_B$ is a steroid selected from the group consisting of stigmasterol, ergosterol and cholic acid;

n is an integer ranging from 1 to about 2,000 where n is greater than 1 only when Z is $Z_{16}$ or $Z_{17}$;

m is 0 or 1, where m is 0 when Z is $Z_{16}$ or $Z_{17}$ and m is 1 when Z is $Z_1$–$Z_{15}$ or $Z_{18}$;

A is selected from any of $A_1$–$A_3$ where $A_1$ is

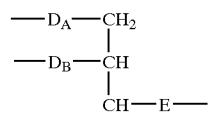

where $D_A$ and $D_B$, independently of one another, are selected from the group consisting of $D_1$–$D_3$ where:
$D_1$ is —$Y_1$—CO—$Y_2$—, where $Y_1$ and $Y_2$, independently of one another, are O and N, wherein at least one of $Y_1$ and $Y_2$ is N;
$D_2$ is —CH=CH—O—;
$D_3$ is —O— or —CO$_2$—; and
wherein E is selected from the group consisting of $E_1$–$E_3$ where:
$E_1$ is

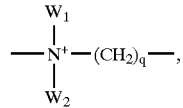

where $W_1$ and $W_2$, independently of one another, are $C_{1-24}$ alkyl, alkenyl or aryl; q is 1 to 6;
$E_2$ is —PO$^-_4$—(CH$_2$)$_n$—NH—, where n is 2–6 with n of 2 being preferred;
$E_3$ is —(PO$^-_4$)$_r$—[inositol]—NH—, where r is 1 or 2;
$A_2$ is

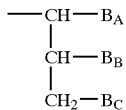

where $B_A$–$B_C$, independently of one another, are selected from the group consisting of the following groups $B_1$–$B_4$, wherein one of $B_A$–$B_C$ is $B_1$, one of $B_A$–$B_C$ is $B_2$, and one of $B_A$–$B_C$ is $B_3$ or $B_4$;

$B_1$ is —OH;
$B_2$ is —NH—R, where R is $C_{1-23}$ alkyl, alkenyl or acyl;
$B_3$ is —O—Z or —NH—Z; and
$B_4$ is —PO$^-_4$—(CH$_2$)$_n$—NH—Z, where n is 2–6 with n of 2 being preferred;
$A_3$ is —NH—CH$_2$— or —CO—N—R$_1$—, where A is —NH—CH$_2$— when R is cholic acid and A is —CO—N—R$_1$— when R is stigmasterol or ergosterol;
where $R_1$ is an alkyl, alkenyl, alkynl, alkoxy, acyl or alkylthio having from 1 to about 24 carbon atoms; and
where Z is selected from the group consisting of $Z_1$–$Z_{17}$ where
$Z_1$ is H except where $W_1$ and $W_2$ are methyl;
$Z_2$ is —(CH$_2$)$_n$—X, where n is 1–24 and X is selected from the group consisting of Br, Cl, I and F;
$Z_3$ is —(CH$_2$)$_n$—NH$_2$, n=1–24;
$Z_4$ is —CH$_2$—NH—(CH$_2$)$_3$—NH—(CH$_2$)$_4$—NH$_2$;
$Z_5$ is —CH$_2$—NH—(CH$_2$)$_3$—NH—(CH$_2$)$_3$—NH—(CH$_2$)$_3$—NH$_2$;
$Z_6$ is —CH$_2$—NH—(CH$_2$)$_n$—NH$_2$, n=2–24;
$Z_7$ is —L—X where L is selected from the group consisting of branched or straight chain alkyl, alkenyl, cycloalkyl, aryl, alkoxy, thioalkyl and thioether groups having from 1 to about 24 carbon atoms, and X is selected from the group consisting of Br, Cl, I, F, NH$_2$ and [(NH$_2$)—(CH$_2$)$_n$]$_m$ where n is 2–24 and m is 1–24;

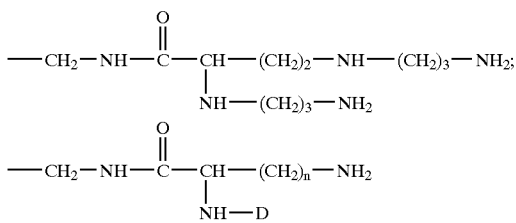

where n=1–24, D is H or other groups attached by amide or alkyl amino groups;
$Z_{10}$ is a reporter molecule;
$Z_{11}$ is a protein, peptide or polypeptide;
$Z_{12}$ is a polysaccharide;
$Z_{13}$ is an amine or halide reactive group;

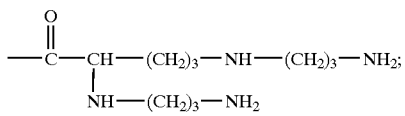

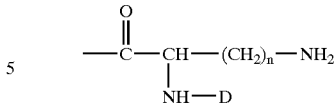

n=1–24, D is H or other groups attached by amide or alkyl amino groups;
$Z_{16}$ is an amino acid;
$Z_{17}$ is a monosaccharide; and
$Z_{18}$ is a nucleic acid binding substance.

Compounds of the invention are useful, either alone or in combination with other lipid aggregate-forming components (e.g., DOPE, DOSPA, DOTMA or cholesterol) for formulation into liposomes or other lipid aggregates. Such aggregates are cationic, able to form stable complexes with anionic macromolecules, such as nucleic acids. The lipid aggregate macromolecular complex interacts with cells making the macromolecule available for absorption and uptake by the cell. The halogenated compounds of the invention are also especially useful as intermediates for chemically coupling the cationic lipid to reporter molecules, proteins, polypeptides, antibodies, polysaccharides and the like to permit targeted delivery, quantitative assessment of targeting, greater efficiency of delivery and enhanced range of delivery capabilities.

Compounds of the invention comprising a nucleic acid binding substance are particularly useful in applications requiring targeted delivery to DNA or RNA. Nucleic acid binding substances include, without limitation, histones, protamines, polycationic peptides, intercalators, polyamines, and nucleic acid binding proteins or domains thereof. Useful nucleic acid binding proteins comprise DNA-binding motifs such as a helix-turn-helix DNA binding motif or a zinc finger. Zinc fingers occur in a variety of eukaryotic transcription factors including Spl, estrogen, and glucocorticoid receptors, several *Drosophila* developmental regulators, *Xenopus* Xfin protein, the *E. coli* UvrA protein, and certain retroviral nucleic acid binding proteins. Compounds of the invention comprising protein, peptide and polypeptide substituents are also useful for binding a variety of other substances. For example, lectins such as concanavalin A and wheat germ agglutinin are useful for binding sugars and β-N-acetylmuranlic acid and α-N-acetylneuraminic acid, respectively.

Compounds of the invention can conjugate to a variety of useful molecules and substances such as polyamines, polyamine acids, polypeptides, proteins, fluorescent dyes, intercalating dyes, reporter molecules, biotin, polysaccharides, monosaccharides, solid support materials, magnetic beads, dendrimer particles, DEAE-Sephadex™ (Pharmacia, Inc.), and the like. Depending on the specific compound of the invention and the substance to be conjugated thereto, conjugation can occur using a compound of the invention as an alkylating agent, using a free amine thereof to react with an amine-reactive group of the substance to be conjugated, or by the use of cross-linking agents.

The present invention also provides compositions and methods for transfecting eukaryotic cells comprising a cationic lipid and an enveloped virus, a component of an enveloped virus, or a fusagenic peptide. Transfecting compositions comprise a cationic lipid compound of the invention in combination with an active or inactive enveloped virus, a viral component of an enveloped virus, or a non-viral fusagenic peptide that functions to facilitate entry of cationic lipid aggregates into the cell. Transfection compositions also optionally contain agents which inhibit lysosomal enzymes or enhance release of material from endosomes, such as chloroquine.

DETAILED DESCRIPTION OF THE INVENTION

The present invention provides novel cationic lipids having unique properties and advantages not heretofore available to the liposome art. The compounds can be used alone or in combination with other compounds, for example, DOPE, to prepare liposomes and other lipid aggregates suitable for transfection or delivery of compounds other than DNA to target cells, either in vitro or in vivo.

Compounds of the invention having a halogen substituent (Z is $Z_2$ or $Z_7$) are additionally useful for synthesis of more complex cationic lipids having the halogen replaced by a desired compound. The convenience of the halogen as a useful leaving group makes such substitutions straightforward. Examples of useful substituents includes without limitation, reporter groups, proteins, peptides, polypeptides, antibodies, carbohydrates, polysaccharides, and the like. Reporter groups can be any readily analyzed or visualized molecule, including, without limitation, fluorescent tags (Fluorescein, rhodamine), luminescent tags (4-methoxy-4-(3-phosphatephenyl)-spiro[1,2-di-oxetane-3,2'-adamantane] (PPD)) biotin, dyes, chelators, affinity probes, etc. Such reporters enable visualization and measurement of target cell-lipid aggregate interactions. Such reporters also provide a means for subsequently accessing targeted cells, by providing surface binding sites unique to targeted cells. In addition, certain drugs and therapeutic compounds can be substituted at the halogen site, by a metabolizable linkage, thereby enhancing efficiency of drug delivery. Also, DNA intercalating compounds and nucleic acid binding substances can be substituted, providing further DNA binding and enhancing transfection efficiency. Compounds such as lectins can be substituted, thereby enhancing the range of delivery capabilities.

Compounds of the invention having ester-amide or amide linked lipophilic groups are particularly useful for applications demanding metabolizable, less toxic compounds. Most of the less toxic lipids currently available contain ester linker bonds, which can be metabolized and catabolized into other lipid species in the treated cells. However, cationic lipids containing ester linker bonds are not stable when stored in an aqueous solution. More stable compounds typically contain ether bonds which are not readily hydrolyzable in the cell. The present invention resolves the problems associated with prior art compounds by providing delivery agents which are stable in aqueous solution, but are metabolizable and thus less toxic to the target cell.

Of those compounds in which the lipophilic group is attached via ester-amide or amide linker bonds, this invention includes, but is not limited to, compounds represented by formulas II and III:

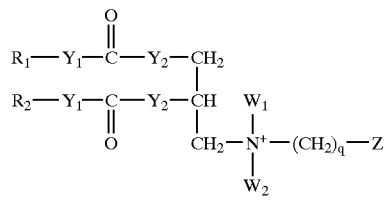

Formula II

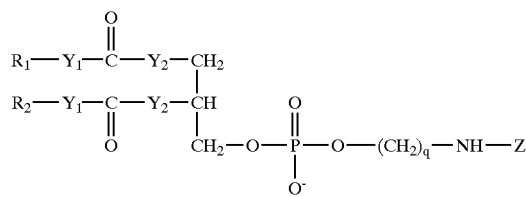

Formula III

In formula II:

$R_1$ and $R_2$, independently of one another, are $C_{1-23}$ alkyl or alkenyl; $Y_1$ and $Y_2$, independently of one another, are O and N, wherein at least one of $Y_1$ and $Y_2$ is N; and $W_1$ and $W_2$, independently of one another, are $C_{1-24}$ branched or straight chain alkyl, alkenyl or aryl; q is 1 to 6; and Z is selected from the group consisting of $Z_1$–$Z_{13}$ and $Z_{18}$ where $Z_1$ is H;

$Z_2$ is —$(CH_2)_n$—X, where n=1–24 and X is selected from the group consisting of Br, Cl, I and F;

$Z_3$ is —$(CH_2)_n$—$NH_2$, n=1–24;

$Z_4$ is —$CH_2$—NH—$(CH_2)_3$—NH—$(CH_2)_4$—$NH_2$;

$Z_5$ is —$CH_2$—NH—$(CH_2)_3$—NH—$(CH_2)_3$—NH—$(CH_2)_3$—$NH_2$;

$Z_6$ is —$CH_2$—NH—$(CH_2)_n$—$NH_2$, n=2–24;

$Z_7$ is —L—X where L is selected from the group consisting of branched or straight chain alkyl, alkenyl, cycloalkyl, aryl, alkoxy, thioalkyl and thioether groups having from 1 to about 24 carbon atoms, and X is selected from the group consisting of Br, Cl, I, F, [$NH_2$ and ($NH_2$)—$(CH_2)_n]_m$ where n is 2–24 and m is 1–24;

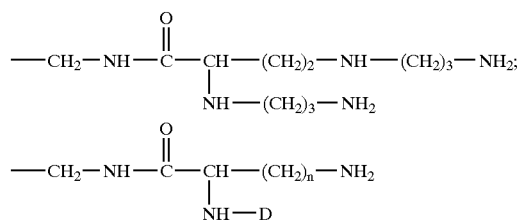

where n 1–24, D is H or other groups attached by amide or alkyl amino groups;

$Z_{10}$ is a reporter molecule;

$Z_{11}$ is a protein, peptide or polypeptide;

$Z_{12}$ is a polysaccharide;

$Z_{13}$ is an amine or halide reactive group; and $Z_{18}$ is a nucleic acid binding substance.

Of particular interest are the products of Formula II in which $W_1$ and $W_2$ are methyl groups and q is 1.

In formula III:

$R_1$, $R_2$, $Y_1$ and $Y_2$ are as defined above for Formula II, q is 2–6 with q of 2 being preferred; and Z is selected from the group consisting of $Z_1$, $Z_3$, $Z_7$, $Z_{10}$–$Z_{12}$, $Z_{14}$–$Z_{15}$, and $Z_{18}$ where $Z_1$ is H, $Z_3$ is —$(CH_2)_n$—$NH_2$, n=1–24, $Z_7$ is —L—X where L is selected from the group consisting of branched or straight chain alkyl, alkenyl, cycloalkyl, aryl, alkoxy, thioalkyl and thioether groups having from 1 to about 24 carbon atoms, and X is selected from the group consisting of Br, Cl, I, F, $NH_2$ and $[(NH_2)$—$(CH_2)_n]_m$ where n is 2–24 and m is 1–24, $Z_{10}$ is a reporter molecule, $Z_{11}$ is a protein, peptide or polypeptide, $Z_{12}$ is a polysaccharide,

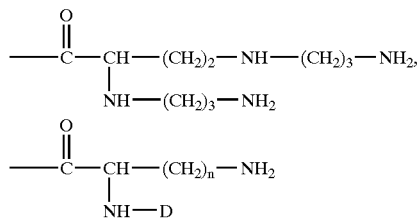

n=1–24, D is H or other groups attached by amide or alkyl amino groups, and $Z_{18}$ is a nucleic acid binding substance.

Compounds of the invention having an enol-ether linked lipophilic group are particularly useful in pH-controlled delivery of macromolecules. The enol-ether compounds of the invention are susceptible to acid hydrolysis but generally stable towards bases. Of those compounds in which the lipophilic group is attached via enol-ether linker bonds, this invention includes, but is not limited to, compounds represented by Formula IV:

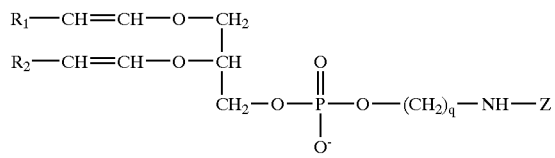

Formula IV

In Formula IV:

$R_1$ and $R_2$, independently of one another, are $C_{1-23}$ alkyl or alkenyl; q=2–6 with q of 2 being preferred; and Z is selected from any of $Z_1$, $Z_3$, $Z_7$, $Z_{10}$–$Z_{12}$ and $Z_{14}$–$Z_{15}$, as defined above for Formula III.

Also included in this invention are compounds of formula I wherein the spacer arm comprises inositol or phosphoinositol. Compounds of the invention having an inositol spacer arm are particularly useful in effectively transfecting cells that contain receptors for inositol phosphates. Since phosphoinositides are found in both plants and animals, the cationic analogues have a broad delivery range. Compounds comprising an inositol or phosphoinositol spacer arm include, but are not limited to, compounds represented by formula V:

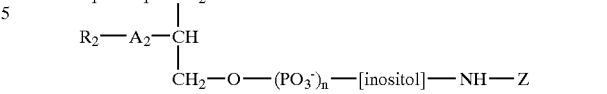

Formula V

In Formula V:

$R_1$ and $R_2$, independently of one another, are $C_{1-23}$ alkyl or n alkenyl; $A_1$ and $A_2$, independently of one another, are —O— or —$CO_2$—; n is 1 or 2, with n of 1 being preferable; and Z is selected from any of $Z_1$, $Z_3$, $Z_7$, $Z10$–$Z12$, $Z_{14}$–$Z_{15}$, and $Z_{18}$, as defined above for Formula III.

Additional subsets of compounds of formula I of this invention include cationic ceramides and sphingolipids. These compounds differ from the cationic lipids currently in use by lacking the glycerol (1,2-propanediol) spacer arm and the linker bond attaching the lipophilic moiety to the spacer arm is an alkyl bond, rather than an easily hydrolyzable bond such as an ester or amide. Since ceramides and sphingolipids are present in nervous tissues, cationic analogues of these compounds are particularly useful for transfecting neural cells. The cationic ceramide and sphingolipid compounds of the invention include, but are not limited to, compounds represented by formula VI:

Formula VI

In Formula VI:

R is a straight-chain or branched alkyl or alkenyl having one to about 24 carbon atoms. Preferred R groups are 1-alkenyl having about 12 to about 22 carbon atoms, with 1-pentadecene being most preferred.

$A_A$–$A_C$, independently of one another, are selected from the group consisting of $A_1$–$A_4$, wherein one of $A_A$–$A_C$ is $A_1$, one of $A_A$–$A_C$ is $A_2$, and one of $A_A$–$A_C$ is $A_3$ or $A_4$, and wherein the groups $A_1$–$A_4$ are as follows:

$A_1$ is OH;

$A_2$ is —NH—R, where R is $C_{1-23}$ alkyl, alkenyl or acyl;

$A_3$ is —O—Z or —NH—Z, where Z is selected from the group consisting of $Z_1$–$Z_{13}$ as defined above for Formula II; and $A_4$ is —$PO^-_4$—$(CH_2)_n$—NH—Z, where n is 1–24, with n of 2 being preferred, Z is selected from any of $Z_1$, $Z_3$, $Z_7$, $Z_{10}$–$Z_{12}$, $Z_{14}$–$Z_{15}$ and $Z_{18}$, as defined above for Formula III.

Also included in this invention are compounds of Formula I wherein the lipophilic group is a steroid, rather than a long-chain hydrocarbon. Preferred steroids include stigmasterol, ergosterol and cholic acid. These compounds are useful in transfecting diverse types of cells. Cationic steroids of the invention include, but are not limited to, compounds represented by formula VII:

Formula VII

In Formula VII:

A is a steroid selected from the group consisting of stigmasterol, ergosterol or cholic acid; B is —NH—$CH_2$— or —CO—N—$R_1$, where B is —NH—$CH_2$— when A is cholic acid and B is —CO—N—$R_1$— when A is stigmasterol or ergosterol; where $R_1$ is an alkyl, alkenyl, alkynyl, alkoxy, acyl or alkythio having from 1 to about 24 carbon atoms; and where Z is selected from any of $Z_3$–$Z_{13}$ and $Z_{18}$ as defined above for general Formula I.

The compounds of the present invention also include those in which the cationic region is an amino acid which is indirectly or directly attached, i.e. with or without a linker group, to the lipophilic moiety. These lipophilic polyamino acids are particularly useful for intracellular delivery of negatively charged macromolecules. This aspect of the invention is based on the premise that polycationic polyamino acids alkylated with long hydrocarbon chains have enhanced affinity for cells, many of which bear a net negative charge, and for various polyanions, such as nucleic acids, relative to normal polyamino acids. Moreover, because of the relatively high lipid content of the alkylated polyamino acids, these compounds interact more strongly with the lipid bilayer of cell membranes than their cognate polyamino acids.

Lipophilic polyamino acids of the invention include, but are not limited to, compounds represented by Formula VIII:

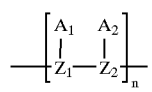

Formula VIII

In Formula VIII:
  $Z_1$ and $Z_2$, independently of one another, are amino acids selected from the group consisting of ornithine, lysine, arginine and histidine;
  n is an integer (chain length) ranging from 1 to about 2,000 with n of between 10 and 50 being preferred.
  $A_1$ and $A_2$, independently of one another, are selected from the group consisting of the following groups $X_1$–$X_6$:
  $X_1$ is a straight-chain alkyl, alkenyl, or alkynyl group having from 2 to about 22 carbon atoms wherein one or more non-neighboring —$CH_2$— groups can be replaced with an O or S atom;
  $X_2$ is a branched alkyl, alkenyl, or alkynyl group having from 2 to about 22 carbon atoms wherein one or more non-neighboring —$CH_2$— groups can be replaced with an O or S atom;
  $X_3$ is a straight-chain or branched alkyl group substituted with one or two OH, SH, $NH_2$ or amine groups within about 3 carbon atoms of the bond between $X_3$ and $Z_1$ or $Z_2$;
  $X_4$ is a substituted straight-chain or branched alkyl, alkenyl or alkynyl group having from 2 to about 22 carbon atoms wherein the substituent is an aromatic, alicyclic, heterocyclic or polycyclic ring and wherein one or more of the non-neighboring —$CH_2$— groups of said alkyl, alkenyl or alkynyl group can be substituted with an O or S atom.
  $X_5$ is a —B—L group wherein B is selected from the group —CO—, —$CO_2$—, —OCO—, —CO—N—, —O—CO—N—, —O—$CH_2$—, —$CH_2$—O—, —S—$CH_2$—, —$CH_2$—S— or —$CH_2$— and L is selected from the group consisting of
    $X_1$, $X_2$, $X_4$, or an aromatic, alicyclic, heterocyclic or polycyclic ring moiety;
  $X_6$ is a —CH(D—L)$_2$ or a —C(D—L)$_3$ group wherein D is selected from the group consisting of —CO—, —$CO_2$—, —OCO—, —CO—N—, —O—CO—N—, —O—, or —S— and L is selected from the group consisting of:
    $X_1$, $X_2$, $X_4$, or an aromatic, alicyclic, heterocyclic or polycyclic ring moiety.

Additional subsets of compounds of Formula I of this invention include those in which the polycationic region is a modified polysaccharide. The lipophilic polycationic polysaccharide compounds of the invention comprise a heteropolysaccharide or homopolysaccharide backbone, preferably a homopolysaccharide such as a glucan or galactan. The polysaccharide comprises between 2 and 2,000 monosaccharides, at least one of which has a cationic substituent. Preferred substituents include tertiary amines, most preferably diethylaminoethyl. Each monomeric unit has between about 3 and about 7 carbon atoms, preferably 3 to 6, and most preferably 6. Preferred polysaccharides include polymers of modified dextrans. Of particular interest are the products of general Formula I in which Z is a modified glucose, m is 0, n is 50 to 600, and R is $C_{2-24}$ alkyl or alkenyl. Most preferred is lipophilic DEAE-dextran. Lipophilic polycationic polysaccharides show increased affinity for negatively charged substances relative to the unsubstituted glycans. Moreover, because of the high lipid content, the modified polysaccharides of the invention interact strongly with the lipid bilayer of cell membranes.

Lipophilic polycationic polysaccharides of the invention include, but are not limited to, compounds represented by Formula IX:

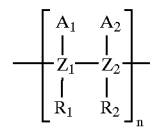

Formula IX where $Z_1$ and $Z_2$, independently of one another, are monosaccharides, preferably glucose; n is an integer (chain length) ranging in value from 1 to about 600, with n of between 50 and 200 being preferred; $R_1$ and $R_2$, independently of one another, are tertiary amines, preferably diethylaminoethyl; and $A_1$ and $A_2$, independently of one another, are selected from the group consisting of groups $X_1$–$X_6$, as defined above for Formula VIII.

This invention also includes lipid aggregates comprising one or more of the compounds of Formulas II–IX or mixtures thereof. Of particular interest are lipid aggregates of the compounds of Formulas II–IX which most closely simulate their naturally occurring counterparts.

The transfection methods of the present invention employing compounds of formulas II–IX or mixtures thereof can be applied to in vitro and in vivo transfection of cells, particularly to transfection of eukaryotic cells including animal cells. The methods of this invention can be used to generate transfected cells which express useful gene products. The methods of this invention can also be employed as a step in the production of transgenic animals. The methods of this invention are useful as a step in any therapeutic method requiring the introduction of nucleic acids into cells. In particular, these methods are useful in cancer treatment, in in vivo and ex vivo gene therapy, and in diagnostic methods. The transfection compositions of this invention can be employed as research reagents in any transfection of cells done for research purposes. Nucleic acids that can be transfected by the methods of this invention include DNA and RNA from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (Ribozymes), and those which function in diagnostic assays.

The compositions and methods provided herein can also be readily adapted in view of the disclosure herein to introduce biologically active anionic macromolecules other than nucleic acids including, among others, polyamines, polyamine acids, polypeptides, proteins, biotin, and polysaccharides into cells. Other materials useful, for example as therapeutic agents, diagnostic materials and research reagents, can be complexed by the cationic lipid aggregates and introduced into cells by the methods of this invention.

The present invention also provides compositions and methods for transfecting cells, preferably eukaryotic cells, comprising a cationic lipid and an enveloped virus, a component of an enveloped virus, a membrane virus, or a non-viral fusagenic compound. These transfecting compositions comprise a cationic lipid compound of the invention in combination with an active or inactive enveloped virus, a viral component of an enveloped virus, or a non-viral fusagenic peptide that functions to facilitate entry of cationic lipid aggregates into the cell.

Viral components of enveloped viruses useful in transfection compositions include viral proteins, envelope fusion peptides, particular viral spike glycoproteins, multimers (i.e., dimers and trimers) thereof, viral peptides of viral spike glycoproteins, and viral envelope fragments containing embedded viral protein. The use of viral components for enhanced transfection is exemplified with an inactive Semliki Forest virus (SFV) particle in co-pending U.S. patent application Ser. No. 08/090,290 (filed Jul. 12, 1993), which is incorporated herein by reference in its entirety. Viruses with a broad host range, such as alphaviruses, are generally preferred. However, viruses which exhibit cell specificity or a specific host range are particularly useful for targeted delivery.

The mechanism of viral enhancement of cationic lipid/DNA complex delivery is not fully understood. After the initial viral recognition of the host cell, certain viruses enter the cell by direct fusion with the cell membrane and, in certain cases, after neuraminidase cleavage of polysaccharides on the cell surface (influenza virus). The viral nucleic acid is then released into the cytoplasm. Other viruses enter the cell through endocytosis and are subsequently released from the endosomal compartment. All steps are protein mediated. Although the mechanism is not understood, these proteins, in conjunction with the cationic lipid/DNA complexes, enhance the uptake of macromolecules by the cell.

Inclusion of an enveloped virus, such as SFV, in a transfection composition with cationic lipid aggregates complexed with nucleic acids thus may enhance transfection compared to transfection mediated by the cationic lipid alone. Enhancement of transfection by alphaviruses, particularly SFV, is pronounced in historically hard-to-transfect cell lines, including human primary cell lines. Enhancement of transfection by enveloped viruses occurs in any cell which the virus can enter and infect. Enhancement of transfection of alphaviruses, particularly SFV, occurs in cells which comprise cholesterol or another 3 β—OH-sterol in their cell membrane. Methods for introducing a sterol or increasing the level of a sterol in cell membranes are known in the art and described in the above-cited patent application (U.S. Ser. No. 08/090,290).

Non-viral fusagenic peptides (or membrane fusion proteins) have been implicated in cell fusion reactions. Although the mechanism is not fully understood, fusagenic peptides can be added to transfection compositions comprising cationic compounds of the present invention to enhance the efficiency of transfection.

The cationic lipids, viral or non-viral enhancing agents and nucleic acid of transfecting compositions can be combined in a variety of ways prior to contact with cells, as described, for example, in the cited copending U.S. application. Transfection compositions also optionally contain agents which inhibit lysosomal enzymes or enhance release of material from endosomes, such as chloroquine.

This invention also includes transfection kits which include one or more of the compounds of formulas II–IV or mixtures thereof as cationic lipids. The invention also includes transfection kits comprising one or more of the compounds of formulas II–IX (or mixtures thereof) in combination with a viral agent, a component of an enveloped virus, or a non-viral fusagenic peptide.

Definitions

Lipid Aggregate is a generic term which includes liposomes of all types both unilamellar and multilamellar as well as micelles and more amorphous aggregates of cationic lipid or lipid mixed with amphiphatic lipids such as phospholipids and steroids.

Target Cell refers to any cell to which a desired compound is delivered, using a lipid aggregate as carrier for the desired compound.

Transfection is used herein to mean the delivery of expressible nucleic acid to a target cell, such that the target cell is rendered capable of expressing said nucleic acid. It will be understood that the term "nucleic acid" includes both DNA and RNA without regard to molecular weight, and the term "expression" means any manifestation of the functional presence of the nucleic acid within the cell including, without limitation, both transient expression and stable expression.

Delivery is used to denote a process by which a desired compound is transferred to a target cell such that the desired compound is ultimately located inside the target cell or in, or on, the target cell membrane. In many uses of the compounds of the invention, the desired compound is not readily taken up by the target cell and delivery via lipid aggregates is a means for getting the desired compound into the cell. In certain uses, especially under in vivo conditions, delivery to a specific target cell type is preferable and can be facilitated by compounds of the invention.

Transfection-enhancing agent as used herein refers to any substance which, when used in conjunction with a cationic lipid, provides significant enhancement of transfection (2-fold or more) over transfection compositions comprising the cationic lipid alone.

Inactive virus refers to a virus which, after exposure to certain chemical or physical conditions, is no longer capable of expressing its viral RNA. Viral inactivation is assessed by exposing viral particles whose RNA contains a reporter gene under the control of the viral subgenomic promoter to potentially inactivating conditions.

Non-viral fusagenic peptides (or membrane fusion proteins) refer to proteins or protein assemblies which interact with lipid components of two opposed bilayers of cell membranes so as to bring about their unification. Although the mechanism is not fully understood, the following non-viral fusagenic compounds have been implicated in cell fusion reactions: melitrin (the principal toxic peptide in bee venom), GALA (a synthetic peptide), snake venom cardiotoxins, snake venom curaremimetic neurotoxins, myelin basic protein, bindin and lysin (proteins from abalone spermatozoa), prostaglandins, FUS1 and FUS2 (products of the FUS1 and FUS2 genes of *Saccharomyces cerevisiae*), PH-30 (a complex of two proteins involved in sperm/egg fusion), members of the cadherin family, and variants of the neural cell adhesion molecule (NCAM). Compounds involved in cell fusion reactions may be added to compositions comprising compounds of the invention, thereby enhancing the efficiency of transfection.

The cationic lipids were prepared by following the general reaction schemes given below (Schemes 1–11).

The quarternized ammonium/carbamate lipids are synthesized as shown in Scheme 1. Alkyl isocyanate treatment of 3-dialkylamino-1,2-propanediol results in the formation of compound 1. Compound 1 is then alkylated with methyl chloride or methyl iodide to obtain compound I (Formula II, $Z=Z_1$). Treatment of compound 1 with dihaloalkane results in compound II. Alkylation of compound 1 with bromoethylphthalamide followed by hydrazinolysis results in compound III (Formula II, $Z=Z_3$) Compounds IV–VI are synthesized by treatment of compound II with the corresponding amine at high temperature. Compounds IX and X are synthesized by condensing compound III with the corresponding amine-protected amino acids and the subsequent removal of the protecting group. Compound XI is synthesized by treating compound III with reporter groups that contain an activated carboxyl group.

The scheme provides a general method for the conjugation of lipids to any molecule or substance of interest. The alkyl halide II can be used as a general alkylating agent. Thus, any molecule of interest that has a nucleophilic moiety can react with compound II (Scheme 2) (J. March (1985) *Advanced Organic Chemistry*, John Wiley & Sons, New York, pp. 364–366; Hilgetag & A. Martini, eds. (1972) *Preparative Organic Chemistry*, John Wiley & Sons, New York, pp. 448–460). Macromolecules that contain amino groups such as proteins and antibodies can be conjugated to lipids in this manner. Smaller molecules that contain amino groups such as intercalators (methidium spermine), fluorescent dyes, nucleotides, nucleosides, amino acids, peptides and other reporter molecules such as biotin can also be conjugated in this manner.

Conversely, compounds III, IX–X, or IV–VI can be used for the conjugation of any molecules of interest that have electrophilic or nucleophilic sites. Compounds III, IX–X, or IV–VI can react with reporter molecules or other desired molecules if these molecules contain carboxylic acid sites, NHS ester or other active groups such as isothiocyanates, alkylhalides or chlorotriazines (Scheme 3) (Keezer, F. and Douraghi-Zdeh, K. (1967) Chem. Rev. 67:107; Dottario-Martin, B. and Ravel, J. H. (1978) Anal. Biochem. 76:562; Staros, J. V. (1982) Biochemistry 21:3950.

Compounds III, IX–X, or IV–VI can also be conjugated with molecules that contain nucleophilic sites such as amines by using cross-linking agents (Scheme 4). Disuccinimidyl suberate can be used to conjugate compounds III, IX–X, or IV–VI to molecules that contain an amino group (Staros, J. V. (1982) Biochemistry 21:3990). Cross-linking agents that contain NHS ester and maleimide can be used to conjugate compounds III, IX–X, or IV–VI to molecules that contain sulfhydryl group (Scheme 4) (Ji, T. H. (1979) Biochem. Biophys. Acta 559:39).

Phosphatidic carbamates (Formula III) are synthesized as shown in Scheme 5. Compound 1 is treated with alkyl isocyanate to give compound 2. Removal of the BOC protecting group from compound 2 gives compound XV. Treatment of compound XV with bromoethylphthalamide followed with hydrazinolysis results in XVI. Compound XVII is obtained by treating XVI with dihaloalkanes. Compounds XVIII and XIX are obtained by coupling XVI with BOC-protected carboxy spermine or other amino acids, followed with the removal of the protecting group. Compound XX is obtained by coupling XVI with proteins or peptides using cross linking agents.

Cationic analogs of sphingolipids wherein $A_A$–$A_C$ are selected from the group consisting of $A_1$–$A_3$ (Formula VI) can be synthesized as described in Scheme 6. Sphingosine (1) is alkylated to give compound 2. The primary hydroxyl group is selectively protected with dimethoxytrityl (DMTR) to obtain compound 3. Compound 3 is alkylated with bromoacetic acid in the presence of base to obtain compound 4. Treatment of compound 4 with diamino alkane in the presence of DCC results in compound 5.

Compound 3 can be acylated with acetyl chloride to obtain compound 9 which, on treatment with acid, yields compound 10. Compound 10 is alkylated with bromoacetic acid followed with treatment with DCC/diamino alkane to obtain compound 12.

Compounds 5 and 12 can be acylated or alkylated as in Schemes 1–5 to obtain analogous compounds. Thus, treatment of compound 5 with BOC-protected carboxy spermine followed with treatment with acid results in the polycationic compound 6. Proteins or polypeptides can be conjugated to compounds 5, 8 or 12 using cross linking agents.

Cationic analogs of sphingolipids wherein one of $A_A$–$A_C$ is $A_4$ (Formula VI) can be synthesized as described in Scheme 7. Compound 1 is selectively acylated using N-hydroxysuccinimide (NHS) esters of fatty acids to obtain compound 2. Selective protection of the hydroxyl groups using dimethoxytritylchloride (DMTrCl) yields compound 3. DCC-mediated coupling of compound 3 with amine-protected aminoalkyl phosphate gives compound 4. Removal of the protecting groups yields compound 5. Compound 5 can be converted to the various analogues using the methods described above in Schemes 3 and 4.

The cationic steroid compounds of the invention are synthesized as shown in Scheme 8. For example, cholic acid is treated with a diaminoalkane in the presence of DCC to obtain compound 2. Compound 2 is then treated with BOC-protected carboxyspermine to give compound 3. Alternatively, compound 2 is conjugated to macromolecules such as proteins, polypeptides, polyamines, and polycationic compounds (see, e.g., group $R_3$ in Scheme 2) by using a cross linking agent. Thus, compound 2 can be treated with cross linkers such as DSS followed with proteins or polypeptides, for example, to obtain compound 4.

Compounds of the invention in which the lipophilic group is attached via an enol-ether linker bond, such as compounds represented by formula IV, are prepared as shown in Scheme 9. Treatment of compound 2 with an aldehyde (1) in the presence of acid followed with dehydration results in compound 3. The ester bond of compound 3 is hydrolyzed with base to obtain the corresponding alcohol 4. Compound 4 is then treated with compound 1 in the presence of acid to obtain compound 5. Amine-protected aminoalcohols (6) are conjugated to compound 5 using DCC as coupling agent to obtain compound 7. Removal of the protecting group from compound 7 yields compound 8. Compound 8 can be further modified as described above for schemes 1–5.

The phosphoinositide lipids (Formula V) are synthesized as shown in Scheme 10. The hydroxyl groups of inositol are protected using standard techniques (see, e.g., J. Chem. Soc. (1987) 423–429) to produce compound 1. Compound 1 is then coupled to compound 2 using DCC as an activator to obtain compound 3. The isopropylidene group of compound 3 is removed with a mild acid to obtain compound 4. Compound 4 is then treated with bromopropylphthalamide to obtain compound 5. Hydrazinolysis of compound 5 results in compound 6. Compound 6 can be further modified, as described above for schemes 1–5, to produce the various compounds of formula V. The phosphoinositide lipids thus can be conjugated to any molecule or substance of interest, as exemplified with the carbamate lipids.

Lipophilic polyamino acids of the invention (Formula VIII) are synthesized as shown, for example, in Scheme 11. Polylysine is partially acylated using compound 2 in the presence of a coupling agent (such as DCC) to produce the corresponding lipophilic polyamino acid. As will be appreciated by those skilled in the art, compound 2 can be any lipophilic moiety comprising an amine-reactive group. Alternatively, the polyamino acid can be modified as described above for Schemes 1–5.

Lipophilic polycationic polysaccharides of the invention (Formula IX) can be similarly synthesized using standard coupling techniques as shown, for example, in Scheme 12. DEAE-dextran is partially acylated with R—CO—OH—DCC, where R is alkyl, alkenyl $C_{12-24}$, and treated with compound 2 in the presence of DCC to obtain compound 3.

The compounds of the invention can be used in the same manner as are prior art compounds such as DOTMA, DOTAP, DOGS and the like. Methods for incorporating such cationic lipids into lipid aggregates are well-known in the art. Representative methods are disclosed by Felgner et al., supra; Eppstein et al. supra; Behr et al. supra; Bangham, A. et al. (1965) M. Mol. Biol. 23:238–252; Olson, F. et al. (1979) Biochim. Biophys. Acta 557:9–23; Szoka, F. et al. (1978) Proc. Natl. Acad. Sci. USA 75:4194–4198; Mayhew, E. et al. (1984) Biochim. Biophys. Acta 775:169–175; Kim, S. et al. (1983) Biochim. Biophys. Acta 728:339–348; and Fukunaga, M. et al. (1984) Endocrinol. 115:757–761. Techniques for preparing lipid aggregates of appropriate size for use as delivery vehicles include sonication and freeze-thaw plus extrusion as perhaps the most commonly used. See, e.g., Mayer, L. et al. (1986) Biochim. Biophys. Acta 858: 161–168. Microfluidization is used when consistently small (50–200 nm) and relatively uniform aggregates are desired (Mayhew, E., supra). Aggregates ranging from about 50 nm to about 200 nm diameter are preferred; however, both larger and smaller sized aggregates are functional.

Methods of transfection and delivery of other compounds are well-known in the art. The compounds of the present invention yield lipid aggregates that can be used in the same processes as those prior art compounds.

Viral components or non-viral fusagenic compounds can be combined with the cationic lipids of the invention to enhance the efficiency of transfection and/or the range of delivery capabilities. Methods for enhancing transfection using fusagenic compounds are well-known in the art. Preferred methods include those disclosed in co-pending U.S. patent application Ser. No. 08/090,290.

It will be readily apparent to those of ordinary skill in the art that a number of general parameters are important for optimal efficiency of transfection or delivery. These parameters include, for example, the cationic lipid concentration, the concentration of compound to be delivered, the medium employed for delivery, the length of time the cells are incubated with the polyanion-lipid complex, and the relative amounts of cationic and non-cationic lipid. It may be necessary to optimize these parameters for each particular cell type. Such optimization is routine employing the guidance provided herein and knowledge generally available to the art.

It will also be apparent to those of ordinary skill in the art that alternative methods, reagents, procedures and techniques other than those specifically detailed herein can be employed or readily adapted to produce the liposomal precursors and transfection compositions of this invention. Such alternative methods, reagents, procedures and techniques are within the spirit and scope of this invention.

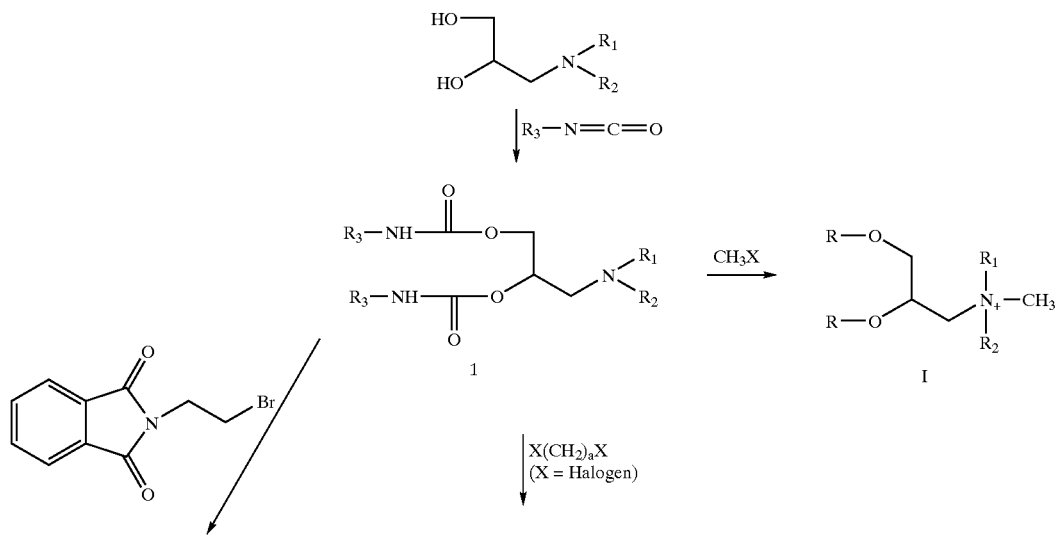

SCHEME 1

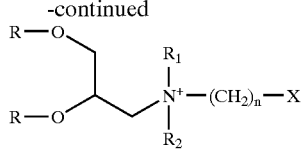
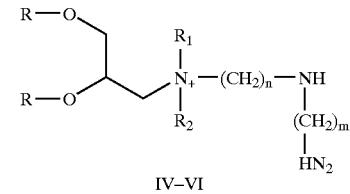
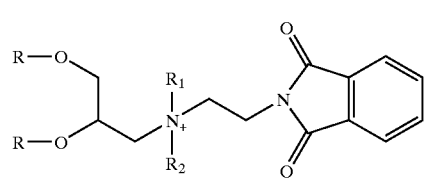
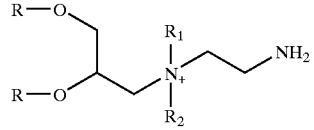
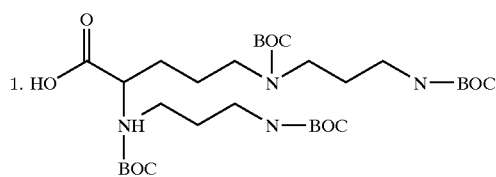
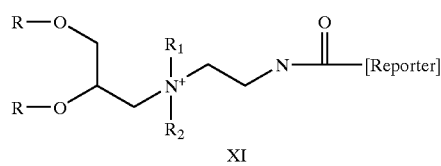
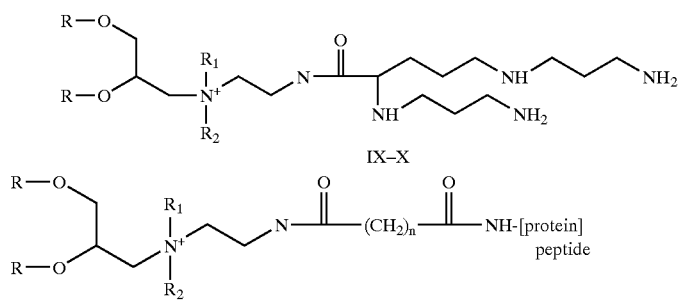
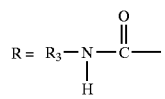
R₁ and R₂ = C₁₋₂₄ alkyl, alkenyl or aryl
R₃ = C₁₋₂₃ alkyl or alkenyl
SCHEME 2
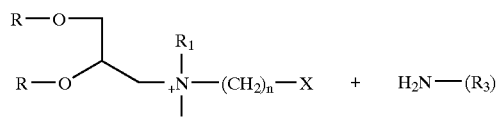
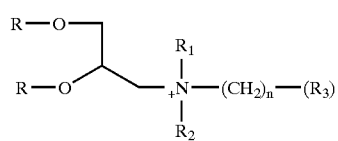
R = C₁₋₂₄ alkyl or alkenyl
R₁ and R₂ = C₁₋₂₄ alkyl, alkenyl or aryl
R₃ = Polyamine
Reporter molecule
Protein
Polysaccharide
Polypeptide
Fluorescent dyes
Intercalators
Polyamino acid
n = 1–24
X = Halogen

SCHEME 3

R = $C_{1-24}$ alkyl or alkenyl $R_1$ and $R_2$ = $C_{1-24}$ alkyl, alkenyl or aryl $R_4$ =

$R_3$ = Polyamine
Reporter molecule
Protein
Polysaccharide
Polypeptide
Fluorescent dyes
Intercalators
Polyamino acid
Solid support
Magnetic beads n = 2–24

SCHEME 4

R = C<sub>1–24</sub> alkyl or alkenyl
R₁ and R₂ = C<sub>1–24</sub> alkyl, alkenyl or aryl
R₃ = Polyamine
    Reporter molecule
    Protein
    Polysaccharide
    Polypeptide
    Fluorescent dyes
    Intercalators
    Polyamino acid
n = 2–24
m = 1–24
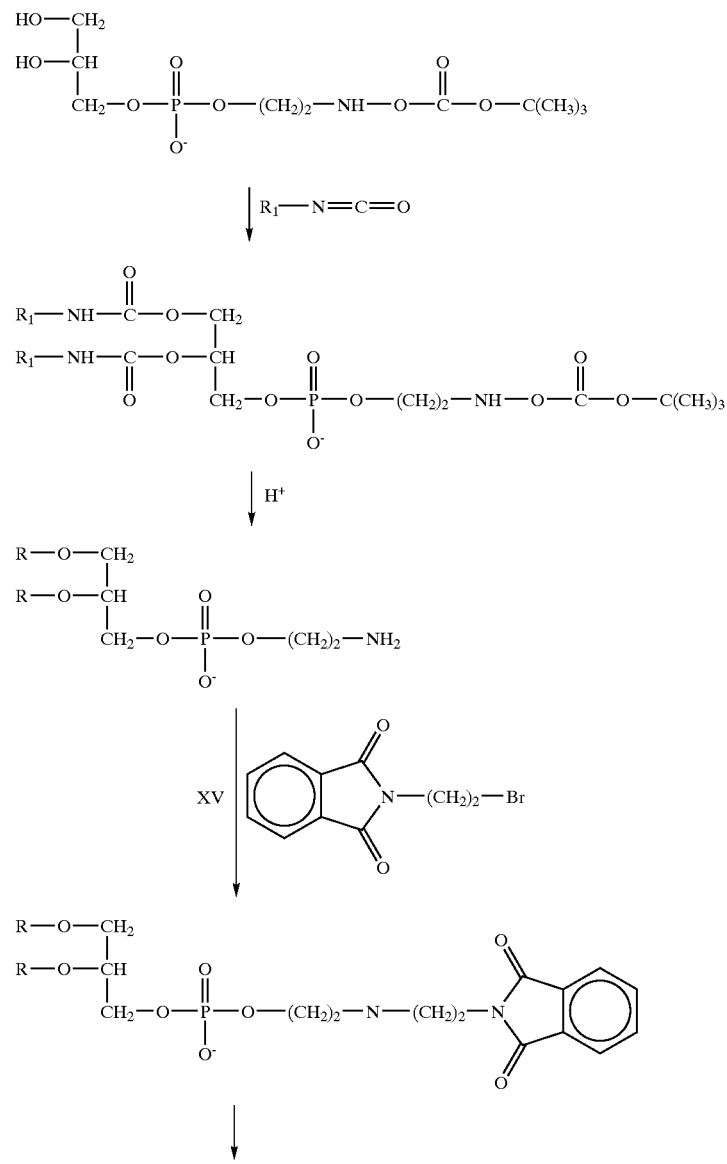
SCHEME 5

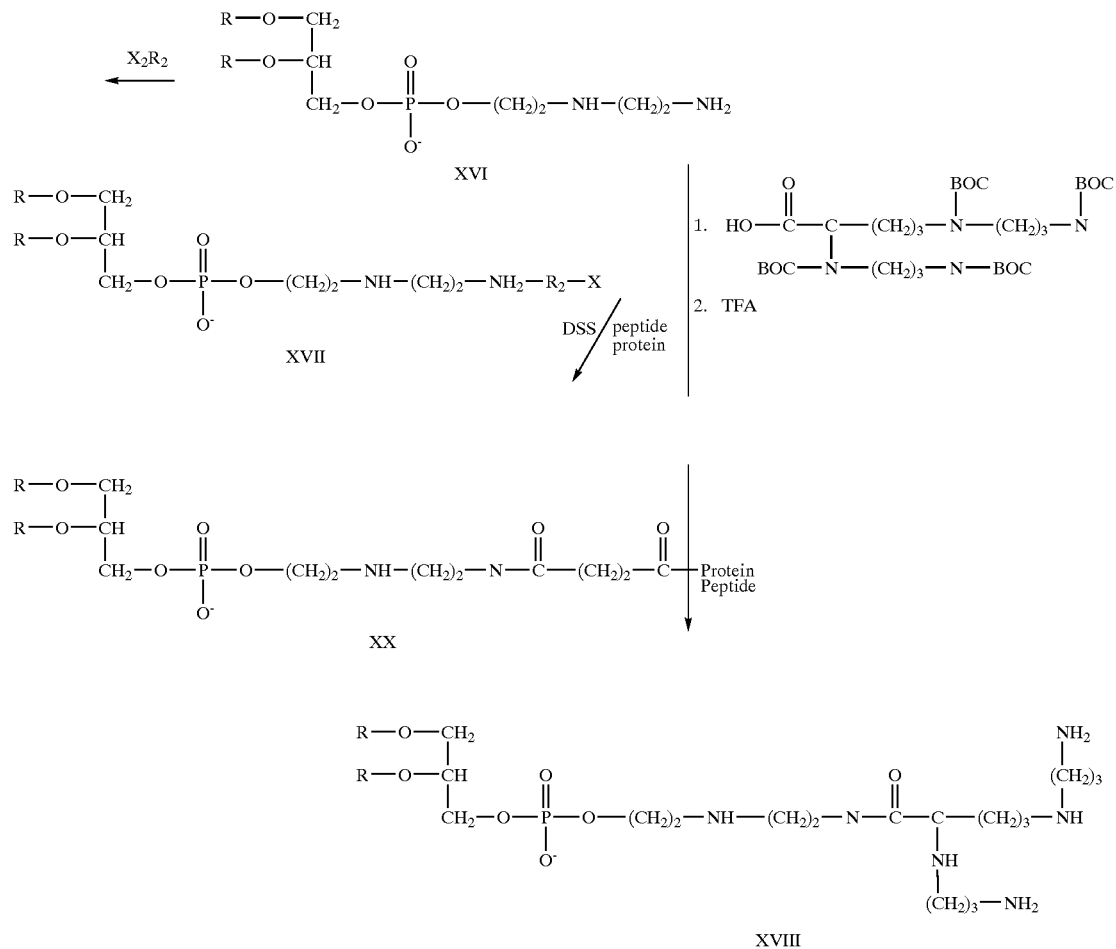
SCHEME 6
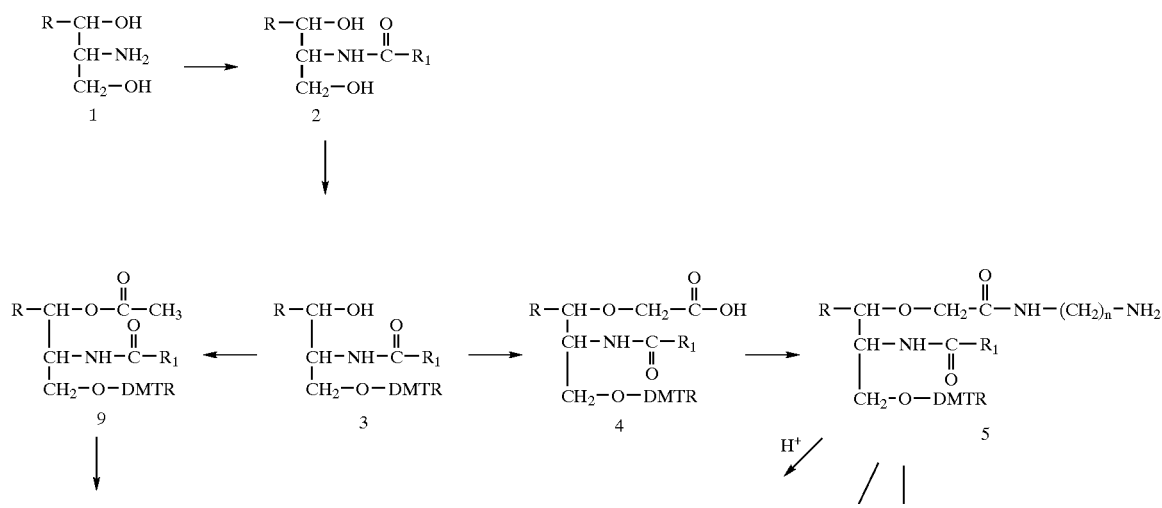

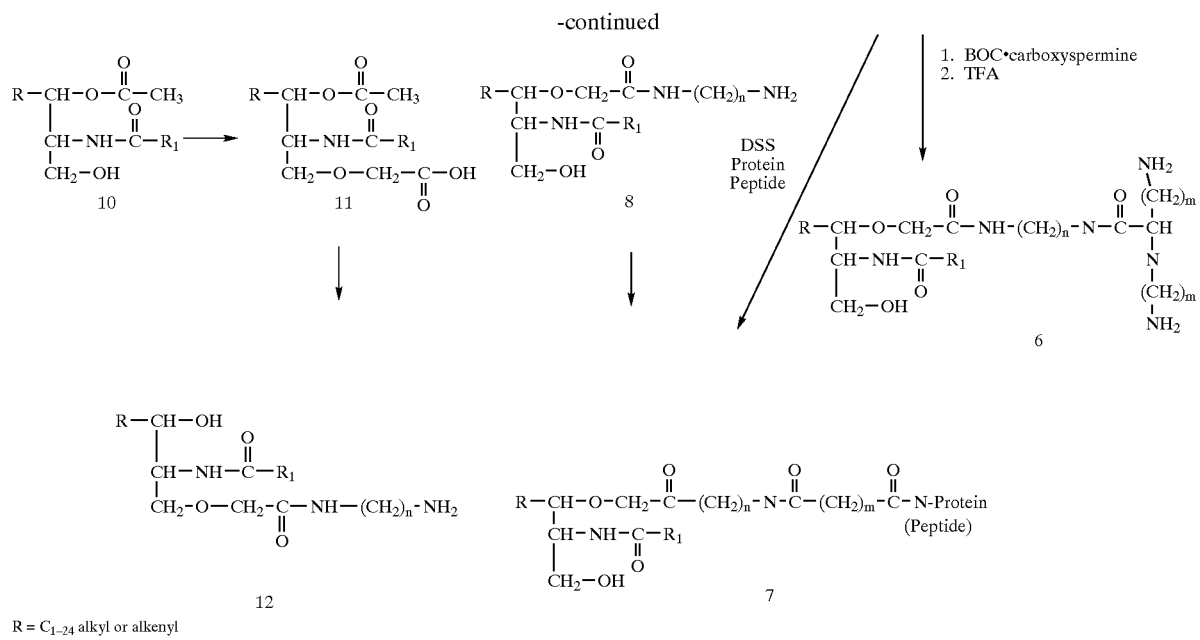
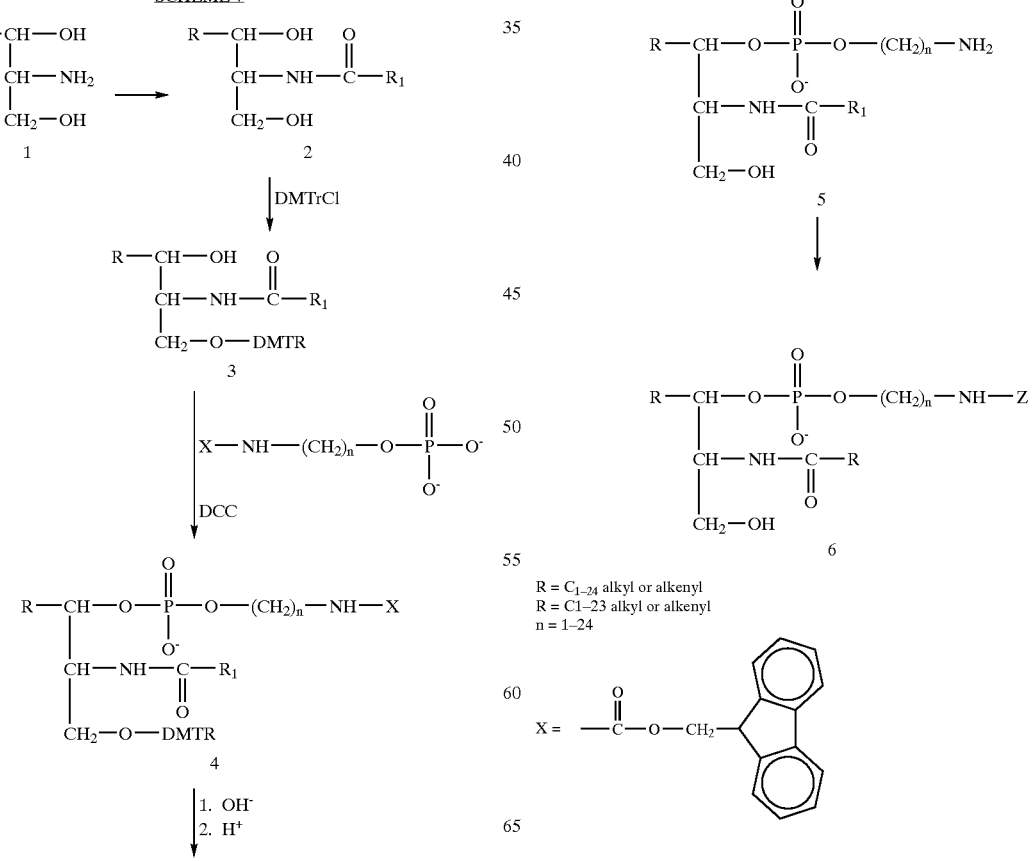

SCHEME 8
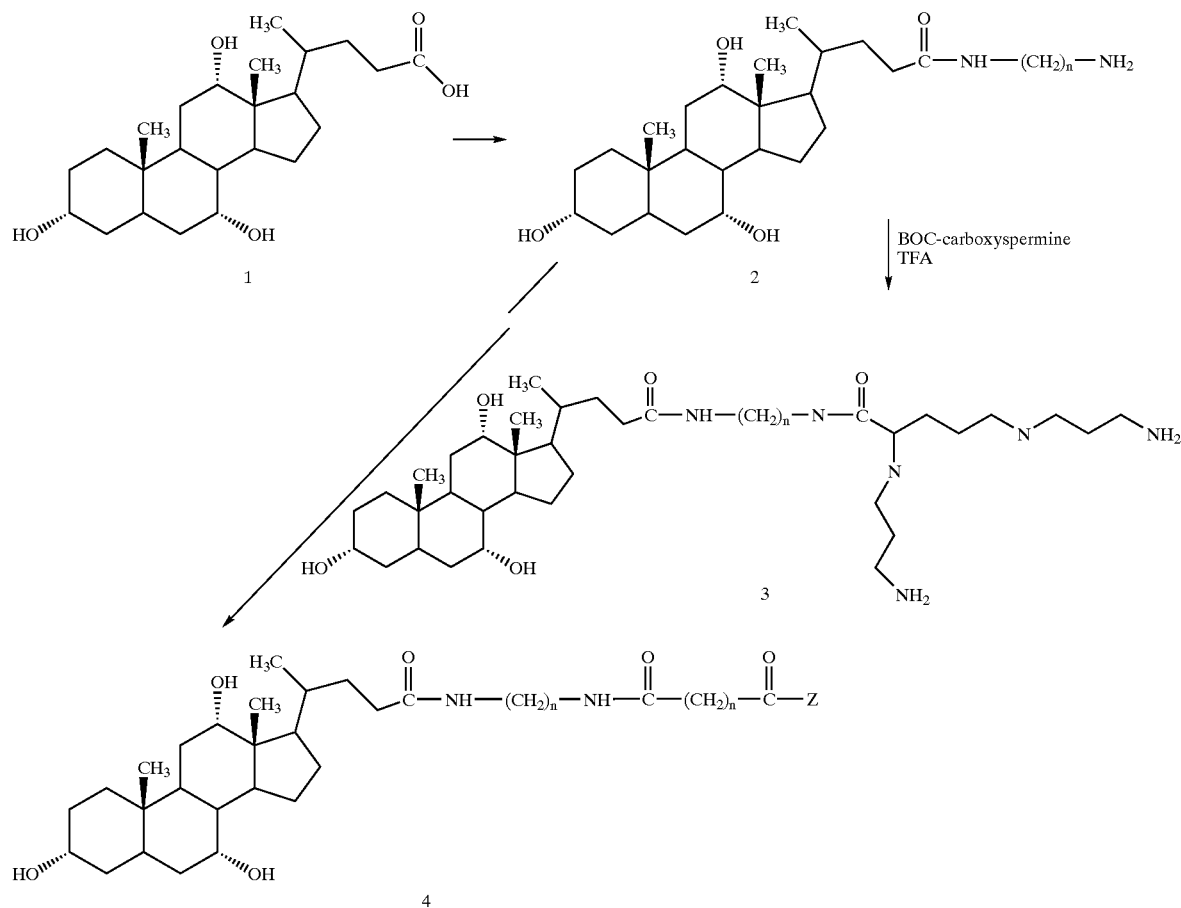
n = 2–24
Z = protein, peptide, polypeptide or polycation
SCHEME 9
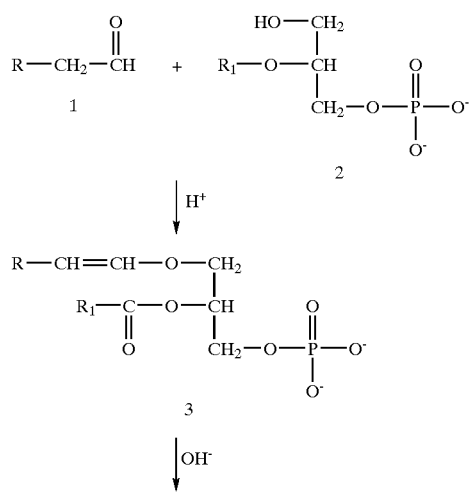

-continued
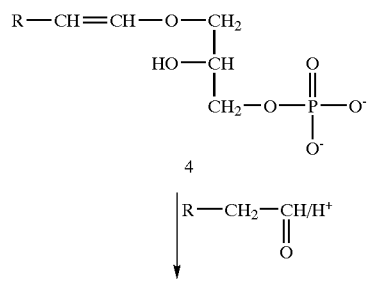
4
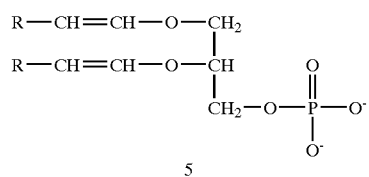
5
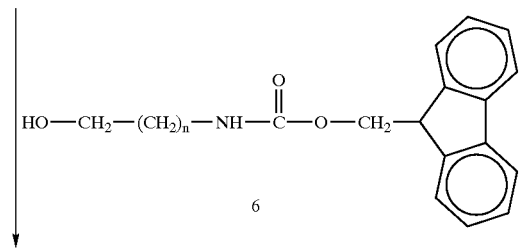
6
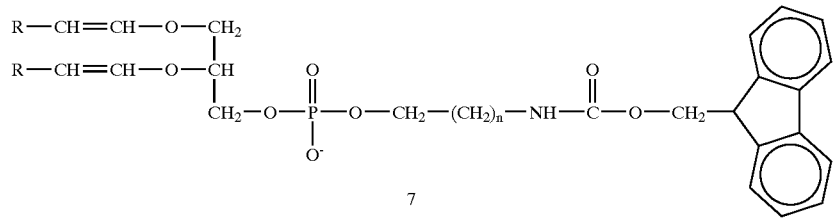
7
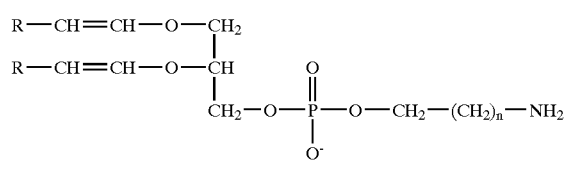
8

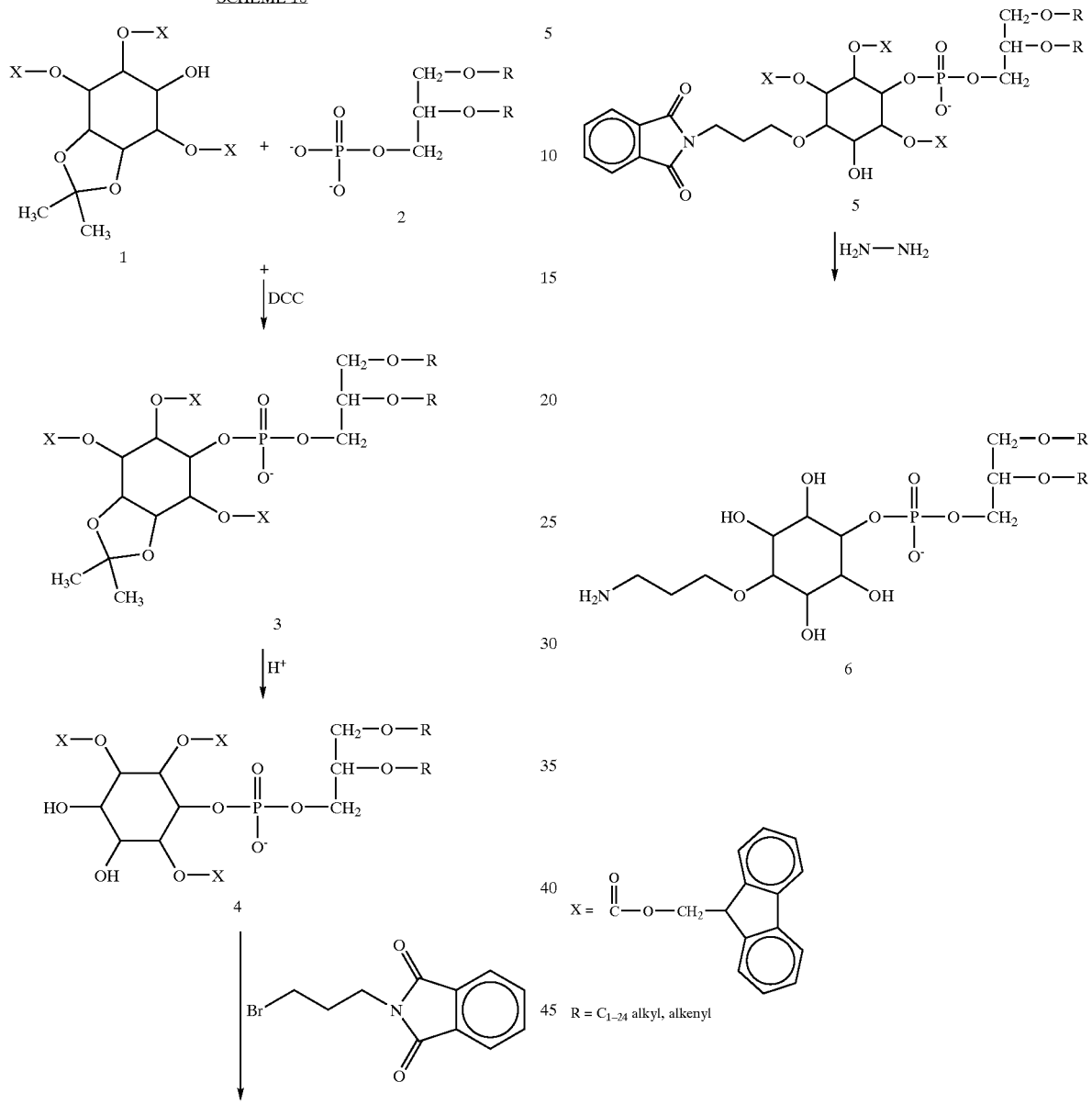
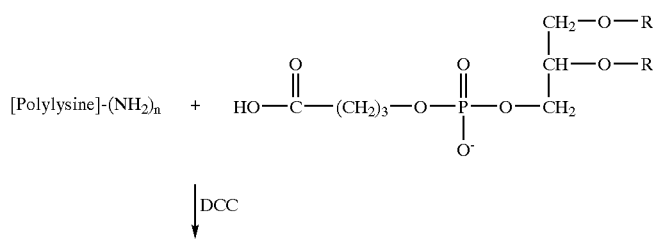

-continued

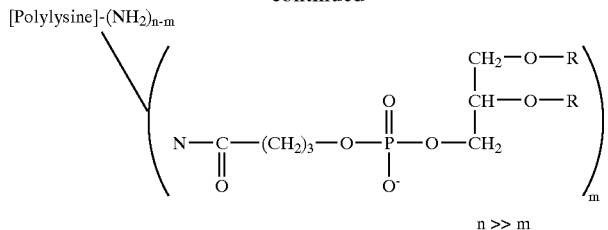

R = C$_{1-24}$ alkyl or alkenyl

SCHEME 12

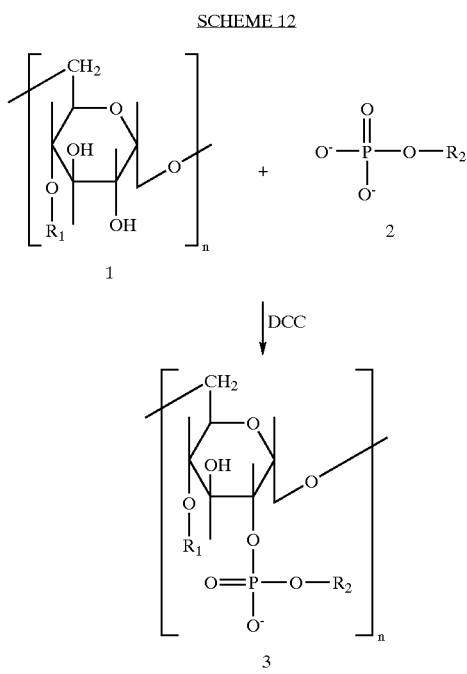

R$_1$ = —CH$_2$—CH$_2$—$^+$NH(CH$_2$CH$_3$)$_2$

R$_2$ = straight chain or branched alkyl, alkenyl, cycloalkyl, aryl, alkoxy, thioalkyl or thioether group having from 12 to about 24 carbon atoms
n = 50–600 (chain length)

What is claimed is:

1. A lipophilic polyamino acid of the formula:

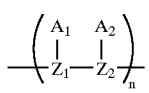

and salts thereof,
where:
Z$_1$ and Z$_2$, independently of one another, are both amino acids selected from the group consisting of ornithine, lysine, arginine and histidine;
n is an integer ranging from 1 to about 2,000;
A$_1$ and A$_2$, independently of one another, are selected from the group consisting of the groups X$_1$–X$_4$ as follows:
X$_1$ is a straight-chain alkyl, alkenyl, or alkynyl group having from 2 to about 22 carbon atoms wherein one or more non-neighboring —CH$_2$— groups can be replaced with an O or S atom;
X$_2$ is a branched alkyl, alkenyl, or alkynyl group having from 2 to about 22 carbon atoms wherein one or more non-neighboring —CH$_2$— groups can be replaced with an O or S atom;
X$_3$ is a straight-chain or branched alkyl group substituted with one or two OH, SH, NH$_2$ or amine groups within about 3 carbon atoms of the bond between X$_3$ and Z;
X$_4$ is a substituted straight-chain or branched alkyl, alkenyl or alkynyl group having from 2 to about 22 carbon atoms wherein the substituent is an aromatic, alicyclic, heterocyclic or polycyclic ring and wherein one or more of the non-neighboring —CH$_2$— groups of said alkyl, alkenyl or alkynyl group can be substituted with an O or S atom; and
the termini of the polyamino acid are an NH$_2$ and a OH.

2. The lipophilic polyamino acid of claim 1 wherein n is between 10 and 50.

3. The lipophilic polyamino acid of claim 1 wherein Z$_1$ and Z$_2$ are lysines.

4. The lipophilic polyamino acid of claim 1 wherein Z$_1$ and Z$_2$ are arginines.

5. The lipophilic polyamino acid of claim 1 wherein A$_1$ and A$_2$, independently of one another, are a straight-chain or branched alkyl, alkenyl, or alkynyl group having from 2 to about 22 carbon atoms wherein one or more non-neighboring —CH$_2$— groups can be replaced with an O or S atom.

6. The lipophilic polyamino acid of claim 5 wherein alkyl, alkenyl, or alkynyl groups have from about 12 to about 22 carbon atoms.

7. The lipophilic polyamino acid of claim 1 wherein the A$_1$ and A$_2$ groups are alkyl groups having from about 12 to about 22 carbon atoms.

8. The lipophilic polyamino acid of claim 1 wherein A$_1$ and A$_2$, independently of one another, are straight-chain or branched alkyl groups substituted with one or two OH, SH, NH$_2$, or amine groups within about 3 carbon atoms of the bond between X$_3$ and Z$_1$ and Z$_2$.

9. The lipophilic polyamino acid of claim 1 wherein A$_1$ and A$_2$, independently of one another, are substituted straight-chain or branched alkyl, alkenyl or alkynyl groups having from 2 to about 22 carbon atoms wherein the substituent is an aromatic alicyclic, heterocyclic or polycyclic ring and wherein one or more of the non-neighboring —CH$_2$— groups of said alkyl, alkenyl or alkynyl group can be substituted with an O or S atom.

10. A composition for transfecting cells which comprises a nucleic acid and one or more lipophilic polyamino acids according to claim 1.

11. The composition of claim 10 wherein the $A_1$ and $A_2$ groups of said lipophilic polyamino acid are alkyl groups having from about 12 to about 22 carbon atoms.

12. A lipid aggregate comprising one or more lipophilic polyamino acids according to claim 1.

13. A method for transfecting a cell which comprises the step of contacting the composition of claim 10 with a cell.

14. A transfection kit which comprises one or more lipophilic polyamino acids according to claim 1.

15. A lipophilic polycationic polysaccharide of formula:

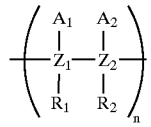

and salts thereof,
where:
$Z_1$ and $Z_2$, independently of one another, are monosaccharides;
n is an integer ranging in value from 1 to about 600;
$R_1$ and $R_2$, independently of one another, are tertiary amines; and
$A_1$ and $A_2$, independently of one another, are selected from the group consisting of groups $X_1$–$X_4$ as follows:
$X_1$ is a straight-chain alkyl, alkenyl, or alkynyl group having from 2 to about 22 carbon atoms wherein one or more non-neighboring —$CH_2$— groups can be replaced with an O or S atom;
$X_2$ is a branched alkyl, alkenyl, or alkynyl group having from 2 to about 22 carbon atoms wherein one or more non-neighboring —$CH_2$— groups can be replaced with an O or S atom;
$X_3$ is a straight-chain or branched alkyl group substituted with one or two OH, SH, $NH_2$ or amine groups within about 3 carbon atoms of the bond between $X_3$ and $Z_1$ and $Z_2$;
$X_4$ is a substituted straight-chain or branched alkyl, alkenyl or alkynyl group having from 2 to about 22 carbon atoms wherein the substituent is an aromatic, alicyclic, heterocyclic or polycyclic ring and wherein one or more of the non-neighboring —$CH_2$— groups of said alkyl, alkenyl or alkynyl group can be substituted with an O or S atom; and
the termini of the polysaccharide are H or OH dependent upon the structures of monosaccharides $Z_1$ and $Z_2$.

16. The polycationic polysaccharide of claim 15 wherein $Z_1$ and $Z_2$ are both glucose.

17. The polycationic polysaccharide of claim 15 wherein n is between 50 and 100.

18. The polycationic polysaccharide of claim 15 wherein $R_1$ and $R_2$ are diethylaminoethyl groups.

19. The polycationic polysaccharide of claim 15 wherein $A_1$ and $A_2$, independently of one another, are a straight-chain or branched alkyl, alkenyl, or alkynyl group having from 2 to about 22 carbon atoms wherein one or more non-neighboring —$CH_2$— groups can be replaced with an O or S atom.

20. The polycationic polysaccharide of claim 15 wherein alkyl, alkenyl, or alkynyl groups have from about 12 to about 22 carbon atoms.

21. The polycationic polysaccharide of claim 15 wherein $A_1$ and $A_2$, independently of one another, are straight-chain or branched alkyl groups substituted with one or two OH, SH, $NH_2$ or amine groups within about 3 carbon atoms of the bond between $X_3$ and $Z_1$ and $Z_2$.

22. The polycationic polysaccharide of claim 15 wherein $A_1$ and $A_2$, independently of one another, are substituted straight-chain or branched alkyl, alkenyl or alkynyl groups having from 2 to about 22 carbon atoms wherein the substituent is an aromatic, alicyclic, heterocyclic or polycyclic ring and wherein one or more of the non-neighboring —$CH_2$— groups of said alkyl, alkenyl or alkynyl group can be substituted with an O or S atom.

23. A composition for transfecting cells which comprises a nucleic acid and one or more polycationic polysaccharides according to claim 15.

24. The composition of claim 23 wherein the $A_1$ and $A_2$ groups of said polycationic polysaccharide are alkyl groups having from about 12 to about 22 carbon atoms.

25. A lipid aggregate comprising one or more polycationic polysaccharides according to claim 15.

26. A method for transfecting a cell which comprises the step of contacting the composition of claim 23 with a cell.

27. A transfection kit which comprises one or more polycationic polysaccharides of claim 15.

* * * * *